United States Patent
Suh et al.

(10) Patent No.: US 10,213,779 B2
(45) Date of Patent: Feb. 26, 2019

(54) PHOTOCATALYTIC FILTER, METHOD FOR MANUFACTURING THE SAME, AND METHOD FOR REACTIVATING THE SAME

(71) Applicant: Seoul Viosys Co., Ltd., Ansan-si (KR)

(72) Inventors: Daewoong Suh, Seoul (KR); Jaeseon Yi, Seoul (KR); Geundo Cho, Ansan-si (KR); Doug Youn Lee, Ansan-si (KR); Hye Kyung Ku, Ansan-si (KR); Kyung Sik Yoon, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 0 days.

(21) Appl. No.: 14/846,562

(22) Filed: Sep. 4, 2015

(65) Prior Publication Data
US 2016/0067698 A1    Mar. 10, 2016

Related U.S. Application Data

(60) Provisional application No. 62/046,114, filed on Sep. 4, 2014.

(30) Foreign Application Priority Data

Mar. 4, 2015    (CN) .......................... 2015 1 0096993

(51) Int. Cl.
*B01J 35/00* (2006.01)
*B01D 46/00* (2006.01)
(Continued)

(52) U.S. Cl.
CPC ........ *B01J 35/004* (2013.01); *B01D 46/0027* (2013.01); *B01D 46/0038* (2013.01);
(Continued)

(58) Field of Classification Search
CPC ........ B01J 35/004; B01J 21/20; B01J 21/063; B01J 38/48; B01J 38/00; B01J 37/0215;
(Continued)

(56) References Cited

U.S. PATENT DOCUMENTS 6,596,915 B1 *  7/2003  Satyapal ................ A62D 3/176
                                              423/245.1
7,740,810 B2    6/2010  Hay et al.
(Continued)

FOREIGN PATENT DOCUMENTS

CN    2747221       12/2005
CN    1958163 A     5/2007
(Continued)

OTHER PUBLICATIONS

Zakersalehi, Photocatalytic Ceramic Membranes, Apr. 2013, Encyclopedia of Membrane Science and Technology, 1, pp. 1-22.*
(Continued)

*Primary Examiner* — James A Fiorito
(74) *Attorney, Agent, or Firm* — Perkins Coie LLP

(57) ABSTRACT

The devices, systems and techniques disclosed in this patent document include photocatalytic filter devices and can be used to provide a method for manufacturing a photocatalytic filter with improved adhesion. In addition, the present disclosure of this patent document includes technology to provide a method for reactivating a photocatalytic filter. Using the disclosed techniques, even if a photocatalytic filter is contaminated, the contaminated photocatalytic filter is easily reactivated while maintaining improved adhesion.

9 Claims, 8 Drawing Sheets

(51) Int. Cl.

| | | |
|---|---|---|
| *B01J 21/06* | (2006.01) | |
| *B01J 21/20* | (2006.01) | |
| *B01J 37/02* | (2006.01) | |
| *B01J 37/08* | (2006.01) | |
| *B01J 38/00* | (2006.01) | |
| *B01J 38/48* | (2006.01) | |
| *A61L 9/20* | (2006.01) | |
| *B01J 21/18* | (2006.01) | |
| *B01J 35/04* | (2006.01) | |

(52) U.S. Cl.
CPC ............ *B01J 21/063* (2013.01); *B01J 21/20* (2013.01); *B01J 35/0013* (2013.01); *B01J 37/0215* (2013.01); *B01J 37/0236* (2013.01); *B01J 37/08* (2013.01); *B01J 38/00* (2013.01); *B01J 38/48* (2013.01); *A61L 9/205* (2013.01); *B01J 21/18* (2013.01); *B01J 35/04* (2013.01)

(58) Field of Classification Search
CPC ... B01J 37/0236; B01J 37/08; B01D 46/0038; B01D 46/0027
See application file for complete search history.

(56) References Cited

U.S. PATENT DOCUMENTS

| 2006/0260995 A1 | 11/2006 | McCormick et al. |
|---|---|---|
| 2009/0162567 A1 | 6/2009 | Tseng et al. |
| 2009/0252655 A1 | 10/2009 | Hsu et al. |
| 2012/0074070 A1 | 3/2012 | Sichel |

FOREIGN PATENT DOCUMENTS

| CN | 1962061 A | * | 5/2007 |
|---|---|---|---|
| CN | 101318127 A | | 12/2008 |
| CN | 102728412 | | 10/2012 |
| JP | 10147771 A | | 6/1998 |
| JP | 2000271491 A | | 10/2000 |
| JP | 2001190952 A | | 7/2001 |
| JP | 200348715 | | 2/2003 |
| JP | 2005532154 A | | 10/2005 |
| JP | 2005349309 A | | 12/2005 |
| JP | 200893630 | | 4/2008 |
| JP | 2009131756 | | 6/2009 |
| JP | 2010215781 | | 9/2010 |
| JP | 2014105150 | | 6/2014 |
| TW | 279175 B | | 6/1996 |
| TW | 200944725 | | 11/2009 |
| TW | 201223643 A | | 6/2012 |
| TW | I4288183 U | | 6/2014 |
| TW | M479924 U | | 6/2014 |
| WO | WO2007026387 | * | 3/2007 |
| WO | 2007/097220 A1 | | 8/2007 |

OTHER PUBLICATIONS

EMTEC, Air Purification Brochure, http://www.emtecproducts.co.uk/pdf/EmtecProductsFilterBrochure.pdf.*
Izadifard et al., Application of photocatalysts and LED light sources in drinking water treatment, 2013, Catalysts, 3, 726-743 (Year: 2013).*
CN 1962061A machine translation (Year: 2007).*
Taiwan Intellectual Property Office, Office Action, TW Application No. 10520557300, dated May 9, 2016, (including English translation), 6 pages.
Office Action, Chinese Patent Application No. 10521172730, dated Sep. 22, 2016, 4 pages.
2nd Office Action in Chinese Patent Application No. 201510096993.1, dated Oct. 11, 2017.
Office Action in Korean Patent Application No. 10-2015-0019753, dated May 18, 2016, 27 pages.
Office Action in Taiwanese Patent Application No. 104131683, dated Jun. 6, 2016, (including English translation), 8 pages.
Office Action, Japanese Patent Application No. 10-2015-186696, dated Sep. 13, 2016, 3 pages.
Office Action in Chinese Patent Application No. 201510633552.0, dated Jun. 5, 2017.
First Office Action in Chinese Patent Application No. 201510096590.7, dated Dec. 26, 2017.
Rudnik, "Optimizing the Design of Room Air Filters for the Removal of Submicrometer Particles," Aerosol Science and Technology, 38:861-869, 2004.
Anandan et al., "Photocatalytic effects of heteropolytungstic acid—encapsulated TiSBA-15 on decomposition of phenol in water," Journal of Photoscience, 2003, vol. 10(3), pp. 231-236.
Kolodzie et al. "Discharge Coefficients Through Perforated Plates" AIChE Journal, (1957), vol. 3, No. 3, pp. 305-312.
Minhua Luo "Practical Technology of Porous Ceramics" China Building Materials Industry Publisher, Mar. 2006, pp. 282-284 and 260-264.
Xianhuai Huang and Yuchao Tang "TiO2 Photocatalysis Technology and Its Application in Environmental Fields" Hefei University of Technology Publisher, Mar. 2013, pp. 43-44.
Wei Chu "Catalyst Engineering" Sichuan University Publisher, Jun. 2006, p. 81.
English translation Summary of Chinese Official Action dated Nov. 16, 2018.

* cited by examiner

PHOTOCATALYTIC FILTER, METHOD FOR MANUFACTURING THE SAME, AND METHOD FOR REACTIVATING THE SAME

CROSS-REFERENCE TO RELATED APPLICATIONS

This application claims priority and benefits of Provisional Application Ser. No. 62/046,114 filed on Sep. 4, 2014, and Chinese Patent Application No. 201510096993.1 filed on Mar. 4, 2015. The entire disclosures of the above applications are incorporated by reference as part of this document.

TECHNICAL FIELD

This patent document relates to a photocatalytic filter device and a technique of manufacturing and reactivating a photocatalytic filter.

BACKGROUND

As used herein, the term "photocatalytic reaction" refers to reactions that use photocatalytic materials such as titanium dioxide ($TiO_2$) or the like. Known photocatalytic reactions include photocatalytic degradation of water, electrodeposition of silver and platinum, degradation of organic materials, etc. Also, there have been attempts to apply such photocatalytic reactions to new organic synthetic reactions, ultrapure water production and the like.

Toxic gases or offensive odor substances, such as ammonia, acetic acid and acetaldehyde, which are present in air, are degraded by the above-described photocatalytic reactions, and air purification devices based on such photocatalytic reactions can be used semi-permanently if they have a light source (e.g., a UV light source) and a filter coated with a photocatalytic material. When the photocatalytic efficiency of the photocatalytic filter has reduced, the filter can be reactivated to restore its photocatalytic efficiency, and then it can be reused. Thus, it can be said that the photocatalytic filter is semi-permanent.

For example, when a UV LED lamp is used as a UV light source, it is advantageous over a conventional mercury lamp or the like in that the UV LED lamp is environmentally friendly. The UV LED lamp does not require toxic gas and is highly efficient in terms of energy consumption, and allows various designs by virtue of its small size.

However, unlike conventional filters such as the pre-filter or HEPA filter, which physically collect large dust particles when air passes therethrough, the photocatalytic filter is configured such that toxic gases adsorbed on the surface of the filter during the passage of air through the filter are degraded by radicals such as $OH^-$, generated by the photocatalytic reaction. Thus, toxic gases in air degraded during the passage of the air through the catalytic filter are not completely degraded, but a portion of the toxic gases is degraded. In other words, the amount of degraded toxic gases in air is gradually increased while the air passes several times through the photocatalytic filter.

Thus, the photocatalytic efficiency of the photocatalytic filter is linked directly with the air cleaning ability of the photocatalytic filter. Toxic gas in a space that uses an air cleaner having high photocatalytic efficiency is degraded faster than toxic gas in a space that uses an air cleaner having the same size and structure but having a relatively low photocatalytic efficiency.

However, if a photocatalytic material in a photocatalytic filter is contaminated, the photocatalytic efficiency will be reduced, and the filter cannot exhibit its function. In this case, the photocatalytic filter generally needs to be replaced. There have been studies on whether a photocatalytic filter can be washed, but the results of the studies mainly indicated that washing of the photocatalytic filter is undesirable, because the washing process is complex and the photocatalytic filter is not easily washed.

SUMMARY

Various embodiments provide an easily regenerable photocatalytic filter, a method for manufacturing the same, and a method for reactivating the same.

In an embodiment, a method for manufacturing a photocatalytic filter is provided to include: dispersing a photocatalytic material; coating a support with the dispersed photocatalytic material; drying the coated support; and sintering the dried support.

In some implementations, the photocatalytic material may include titanium dioxide ($TiO_2$).

In some implementations, the support may include a porous ceramic material.

In some implementations, the sintering may be performed at a temperature of 400 to 500° C. for 1-3 hours, preferably 2-3 hours.

In another embodiment, a photocatalytic filter is provided to include a porous ceramic support, and dispersed $TiO_2$ nanoparticles coated on the support.

In some implementations, the $TiO_2$ nanoparticles coated on the porous ceramic support are those sintered for from one to three hours at a temperature between 400° C. and 500° C.

In some implementations, the photocatalytic filter may comprise a plurality of adjacent parallel cells that form an air flow path in a direction facing UV LED for photocatalytic activation.

In some implementations, the photocatalytic filter comprises a plurality of adjacent parallel cells that form an air flow path in a direction facing UV LED for photocatalytic activation.

In some implementations, the photocatalytic filter has a height of 2 to 15 mm.

In some implementations, a frame between the cells has a thickness of 0.3 to 1.2 mm.

In some implementations, each of the cells has a width of 1 to 4 mm.

In some implementations, the cells has a density of 30 to 260 cells/inch$^2$.

In still another embodiment, a method of reactivating a photocatalytic filter is provided to include: treating a contaminated photocatalytic filter with boiling water, and/or microwaving the treated photocatalytic filter, wherein the photocatalytic filter includes a support coated with dispersed $TiO_2$ nanoparticles.

In some implementations, the support includes porous ceramic, and the $TiO_2$ nanoparticles coated on the support are those sintered for from one to three hours at a temperature between 400° C. and 500° C.

DETAILED DESCRIPTION

Figure 1:
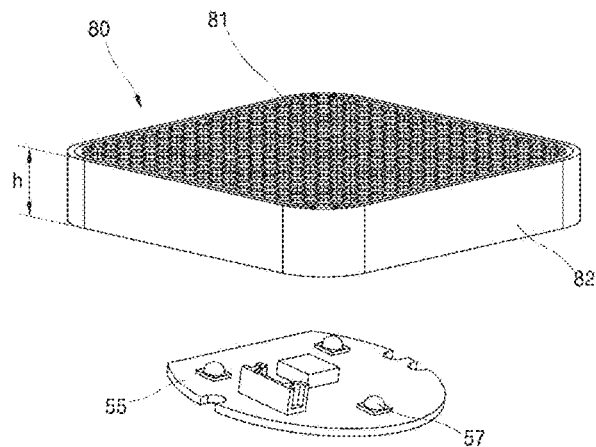
FIG. 1 is a perspective view showing an arrangement of an exemplary photocatalytic filter and a UV LED substrate.

The devices, systems and techniques disclosed in this patent document provide photocatalytic filter devices and a method of manufacturing a photocatalytic filter with improved adhesion.

In addition, the present disclosure of this patent document includes technology to provide a method for reactivating a photocatalytic filter. Using the disclosed techniques, even if a photocatalytic filter is contaminated, the contaminated photocatalytic filter is easily reactivated while maintaining improved adhesion.

The devices, systems and techniques in this patent document are disclosed by examples in the following descriptions and claims.

Hereinafter, embodiments of the disclosed technology will be described in detail with reference to implementation examples, including those illustrated in the accompanying drawings.

The following embodiments are provided by way of examples so as to facilitate the understanding of various implementations of the disclosed technology to those skilled in the art.

Accordingly, the present disclosure is not limited to the embodiments disclosed herein and can be implemented in different forms. In the drawings, widths, lengths, thicknesses, and the like of elements may be exaggerated for convenience and illustrative purposes.

Photocatalytic Filter—Device

Hereinafter, an example of a photocatalytic filter is provided. The photocatalytic filter includes a support, and dispersed $TiO_2$ nanoparticles coated on the support.

The support may include a metal, activated carbon, or ceramic. In one implementation, a porous ceramic honeycomb support may be used as the support. In this case, the porous ceramic honeycomb support helps $TiO_2$ nanoparticles to permeate the ceramic pores during the coating process. Further, $TiO_2$ nanoparticles are anchored through the drying process that will be discussed later in detail, and thus, adhesion of the $TiO_2$ nanoparticles to the support is enhanced.

If a metal material is used as the support, $TiO_2$ nanoparticles are not as easily attached to the photocatalytic support as the porous ceramic honeycomb support. Further, although activated carbon has pores, the activated carbon may be easily damaged during the sintering process.

As will be discussed later in detail, the support may be coated with dispersed $TiO_2$ nanoparticles, thereby providing a photocatalytic filter with improved adhesion.

Figure 2:
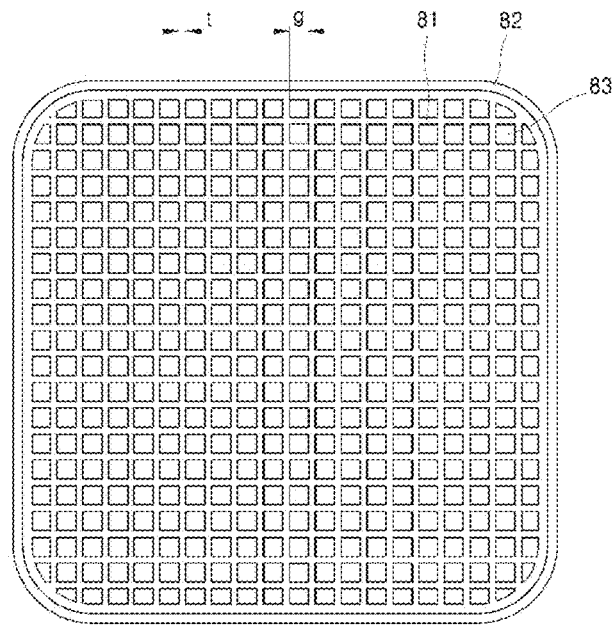
FIG. 2 is a top view of an exemplary photocatalytic filter.

FIG. 1 is a perspective view showing the arrangement of the photocatalytic filter 80 and the UV LED substrate 55, and FIG. 2 is a top view of the photocatalytic filter 80.

Referring to FIG. 1, the UV LED 56 for sterilization is disposed on the central portion of the UV LED substrate 55, and three UV LEDs 57 for photocatalytic activation are disposed around the UV LED 56. In some implementations, the UV LEDs 57 for photocatalytic activation will irradiate UV light toward the photocatalytic filter 80.

As shown in FIG. 2, the photocatalytic filter 80 includes a catalyst portion 81 obtained by sintering $TiO_2$ (titanium dioxide) coated on a ceramic porous material having a check lattice pattern, and an elastic bumper 82 covering the side of the catalyst portion.

Figure 3:
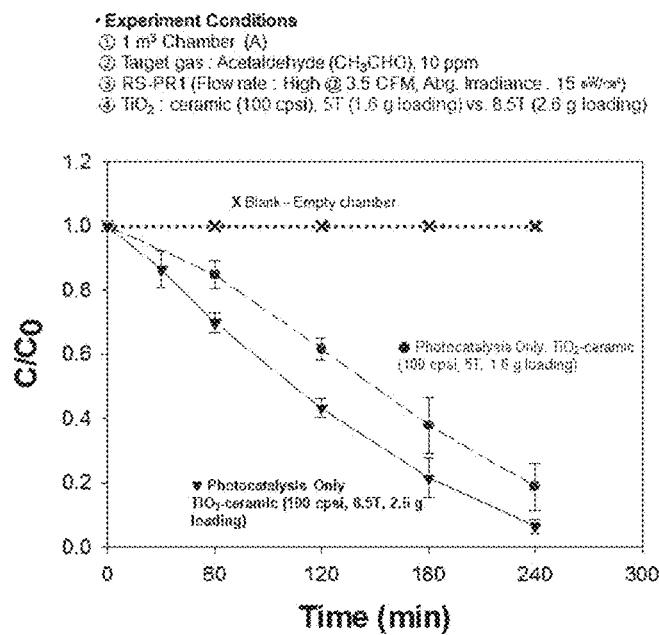
FIG. 3 is a graph showing the change in removal rate of acetaldehyde with a change in the height of a photocatalytic filter.
Figure 4:
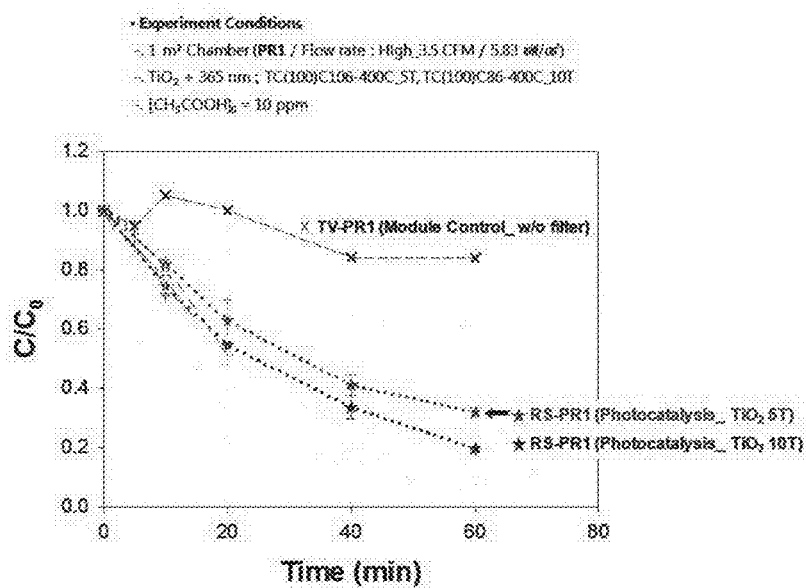
FIG. 4 is a graph showing the change in removal rate of acetic acid with a change in the height of a photocatalytic filter.

FIG. 3 is a graph showing removal rates of acetaldehyde of two photocatalytic filters that have different heights (h), and FIG. 4 is a graph showing removal rates of acetic acid of two photocatalytic filters that have different height (h).

The results of the experiment indicated that, in the case of the photocatalytic filter having the shape shown in FIG. 2, the surface area of the photocatalyst, which increases due to the thickness (t) of the frame between the cells of the photocatalytic filter, did not substantially influence the deodorization efficiency of the photocatalytic filter, but the height (depth) of the photocatalytic filter influenced the inner wall area of the internal air flow path, thus directly influencing the area of contact with air.

Thus, it could be seen that, when the height of the photocatalytic filter was 5-10 mm, the deodorization efficiency of the photocatalytic filter was the highest. In addition, when the height decreases to 2 mm or less, the photocatalytic filter is difficult to use, due to its weak strength, and when the height is 15 mm or more, air resistance merely increases, UV light does not reach the rear portion of the photocatalytic filter or the intensity thereof becomes very weak, and thus only the cost increases without increasing the deodorization efficiency.

Also, it could be seen that, when the width (g) of each cell 83 was 2 mm, the air resistance did not increase, and the rate of shadowed area of the inner wall of the photocatalytic filter, which is generated by the shape of the filter itself blocking UV light irradiated thereto, was not high, suggesting that the cell width of 2 mm is most suitable for maximizing the rate of UV light irradiated area of the inner wall of the photocatalytic filter. Meanwhile, when the cell width decreased to 1 mm or less, the air resistance increased, and the amount of UV light reaching the inner wall decreased, suggesting that the efficiency of deodorization was low. In addition, when the cell width was 4 mm or more, the whole area of the inner wall decreased due to low cell density, which suggests that the efficiency of deodorization was low.

Regarding the density of cells in view of width (g) of each cell above mentioned, when the density of cells was lower than 30 cells/inch$^2$ or less, that is, the cell width increased to 4 mm or more, the area of the inner wall decreased. This indicates that the efficiency of deodorization was low. When the density of cells was 260 cells/inch$^2$ or more, that is, the cell width decreased to 1 mm or less, the air resistance increased and the amount of UV light reaching the inner wall decreased. This indicates that the efficiency of deodorization was low. When the density of cells was about 100 cells/inch$^2$, the air resistance did not increase, and the rate of shadowed area of the inner wall of the filter, which is generated by the shape of the filter itself blocking UV light irradiated thereto, was not high. This suggests that the efficiency of deodorization was the highest.

The results of an experiment on the thickness (t) of the cell frame indicated that, when the frame thickness was 0.3 mm or less, the $TiO_2$ layer became too thin, and thus the photocatalytic efficiency decreased and the strength was insufficient. When the frame thickness was 1.2 mm or more, the material cost increased without increasing the photocatalytic efficiency. In addition, the photocatalytic efficiency was the highest when the frame thickness was 0.6 mm.

Photocatalytic Filter—Fabrication Process

Hereinafter, an example of a method of manufacturing a photocatalytic filter will be discussed.

The photocatalytic filter may be provided by dispersing titanium dioxide ($TiO_2$) nanoparticles, coating a support with the dispersed $TiO_2$ nanoparticles, drying the coated support and sintering the dried support.

As one example, the dispersing process is performed using P25 $TiO_2$ nano-powders commercially available from Evonik Degussa. For example, P25 $TiO_2$ nano-powders may be added into water into which silicon dispersing agent with a concentration between 0.1 and 10% may be dissolved. After dispersing P25 $TiO_2$ nano-powders using a mill, a solid $TiO_2$ nano solution with a concentration from 20 to 40% may be obtained. The dispersing agent including one or more types of components may be used.

During the coating process, if the porous ceramic honeycomb support is selected, the porous ceramic honeycomb support is dip-coated with the prepared $TiO_2$ dispersion liquid. At the time of dip-coating, one to five minutes suspension may be applied such that $TiO_2$ dispersion liquid is sufficiently absorbed by the pores of the porous ceramic honeycomb support.

The drying process may be performed for a predetermined time in a condition that the coated support is maintained at a predetermined temperature. In one implementation, if the porous ceramic honeycomb support is selected, the coated porous honeycomb ceramic support may be maintained in a drying unit at a temperature between 150° C. to 200° C. for three to five minutes.

The sintering process may be performed by maintaining the dried support at a predetermined temperature for a predetermined time. In one implementation, if the porous ceramic honeycomb support is selected, the sintering process may be performed for from two to three hours at between 400° C. and 500° C. Upon our experiments, if the sintering temperature is lower than 300° C., the coated $TiO_2$ photocatalyst is separated easily from the support. If the sintering temperature is higher than 500° C., the crystal structure of the coated $TiO_2$ photocatalyst changes and thus, the photocatalyst activation deteriorates. Thus, in order to provide a photocatalytic filter with improved adhesion and photocatalyst activation, the sintering process may be performed at between 400° C. and 500° C.

Reactivated Photocatalytic Filter

Figure 5:
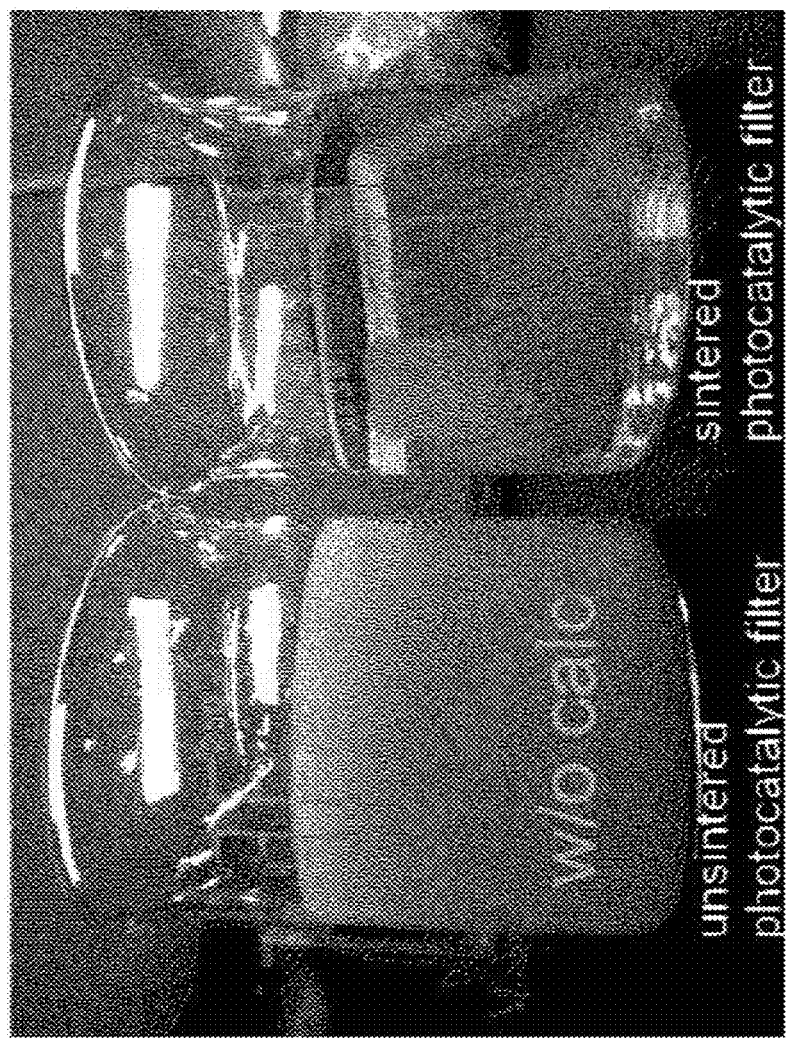
FIG. 5 is a photograph showing the state of a conventional photocatalytic filter and a photocatalytic filter provided according to the present disclosure.

FIG. 5 shows the results of an experiment conducted to examine the adhesion of a catalytic material to a support in a $TiO_2$ photocatalytic filter. In the experiment, each of sintered and unsintered photocatalytic filters was dipped in distilled water, and then sonicated.

As can be seen in FIG. 5, unlike the case of the sintered photocatalytic filter, $TiO_2$ attached to the unsintered photocatalytic filter was eluted into water by sonication.

Figure 6:
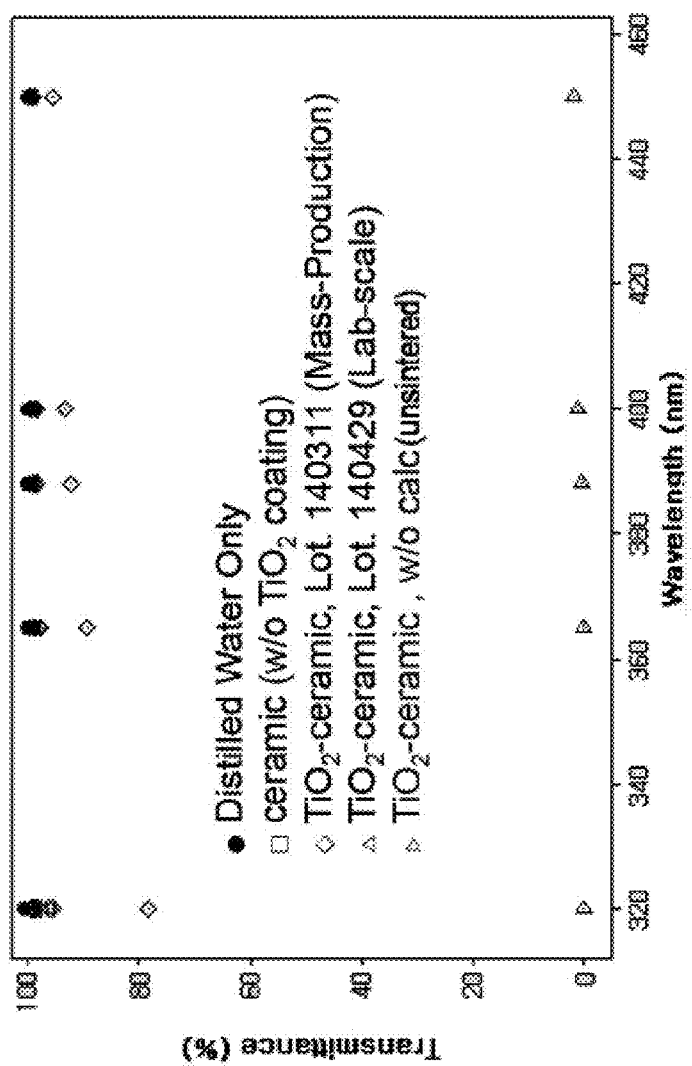
FIGS. 6 and 7 are graphs showing the transmittance of water boiled with each of various filters added thereto.

FIG. 6 shows the transmittance of distilled water, which was measured at various wavelengths in each of the following cases: sonicating distilled water only; adding to distilled water a porous ceramic material not coated with a $TiO_2$ photocatalytic material and then sonicating the distilled water; adding to distilled water a porous ceramic material coated with a $TiO_2$ photocatalytic material and sintered and then sonicating the distilled water; and adding to distilled water a porous ceramic material coated with a $TiO_2$ photocatalytic material but not sintered and then sonicating the distilled water. The transmittance was measured by UV-Vis Spectroscopy (detector: Analytik Jena).

As can be seen in FIG. 6, the transmittance of the water containing the porous ceramic material, which was coated with the $TiO_2$ photocatalytic material and sintered, was nearly similar to that of distilled water. This suggests that the photocatalytic material had excellent adhesion to the porous ceramic material, and that the photocatalytic material was not substantially eluted.

This result indicates that the photocatalytic filter manufactured according to the method of the present disclosure maintains the adhesion of the photocatalytic material to the surface of the photocatalytic filter even when the photocatalytic filter is sonicated.

Figure 7:
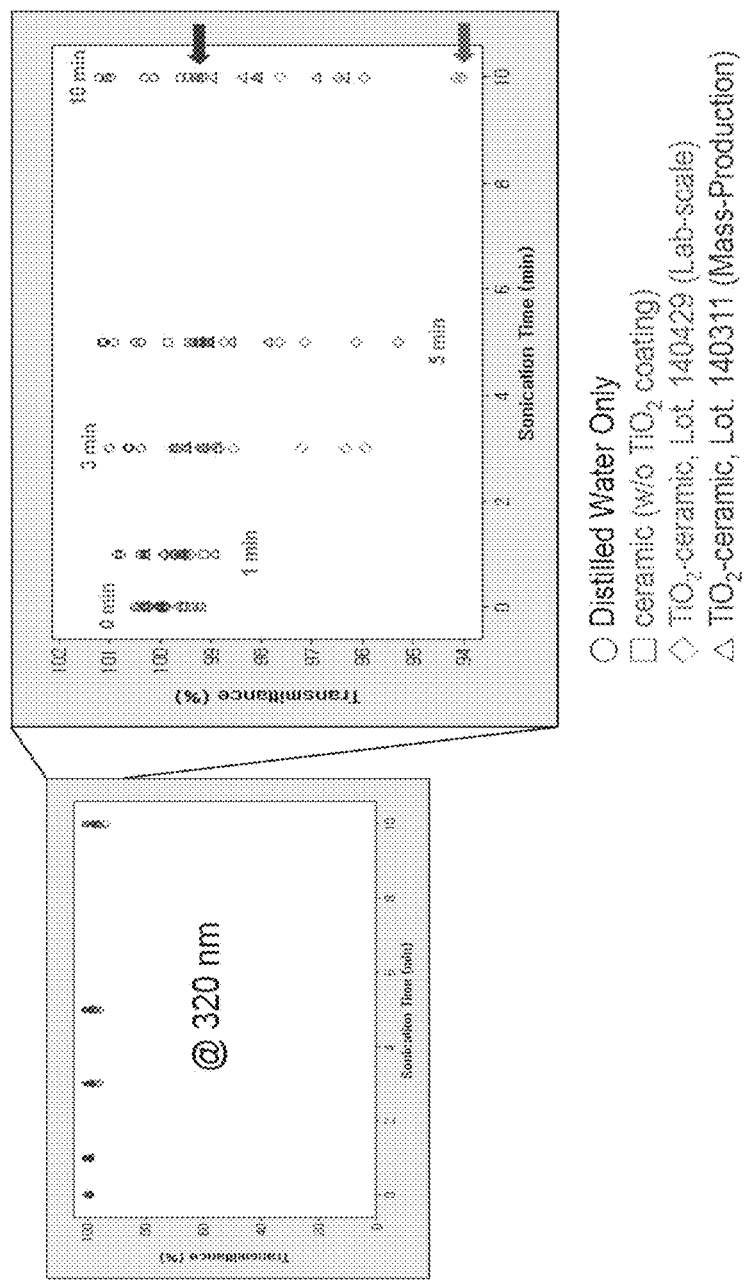

FIG. 7 shows the transmittance of water measured as a function of sonication time in each of the following cases: sonicating distilled water only; adding to distilled water a porous ceramic material not coated with a $TiO_2$ photocatalytic material and then sonicating the distilled water; and adding to distilled water a porous ceramic material coated with a $TiO_2$ photocatalytic material and sintered and then sonicating the distilled water.

As can be seen in FIG. 7, in the case in which the porous ceramic material, coated with the $TiO_2$ photocatalytic material and sintered, was added to distilled water and sonicated, the transmittance of the distilled water showed a tendency to decrease as the sonication time increased, but this decrease in transmittance was not visually distinguishable from distilled water only.

Figure 8:
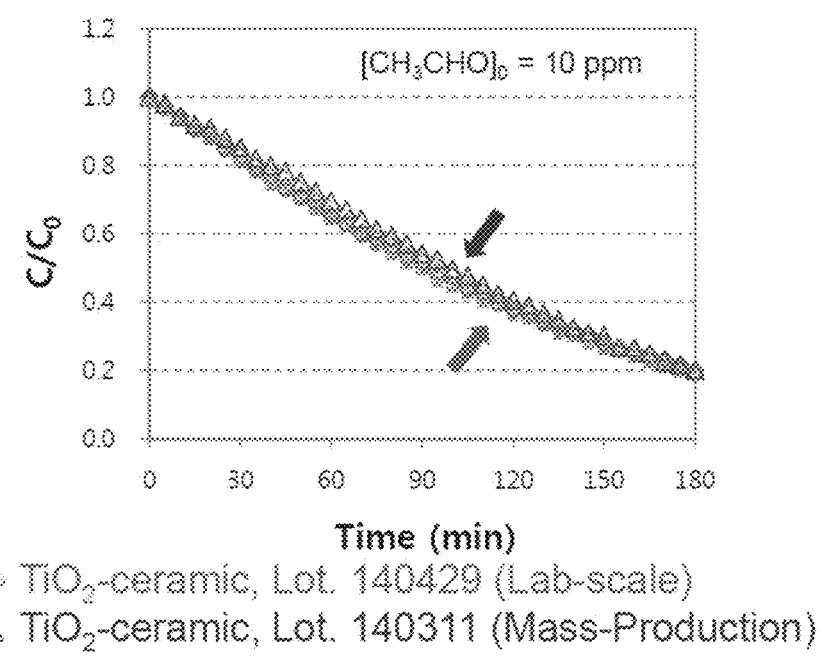
FIG. 8 is a graph showing the results of cleaning air by filters reactivated using boiling water.

FIG. 8 shows the results of measuring the acetaldehyde removal activities of the two samples (see the arrows in FIG. 7) showing the greatest difference in transmittance therebetween among the samples of FIG. 7, after naturally drying the two samples for use as photocatalytic filters. As can be seen in FIG. 8, there was little or no difference in photocatalytic activity between the two samples showing different transmittances as shown in FIG. 7.

Figure 9:
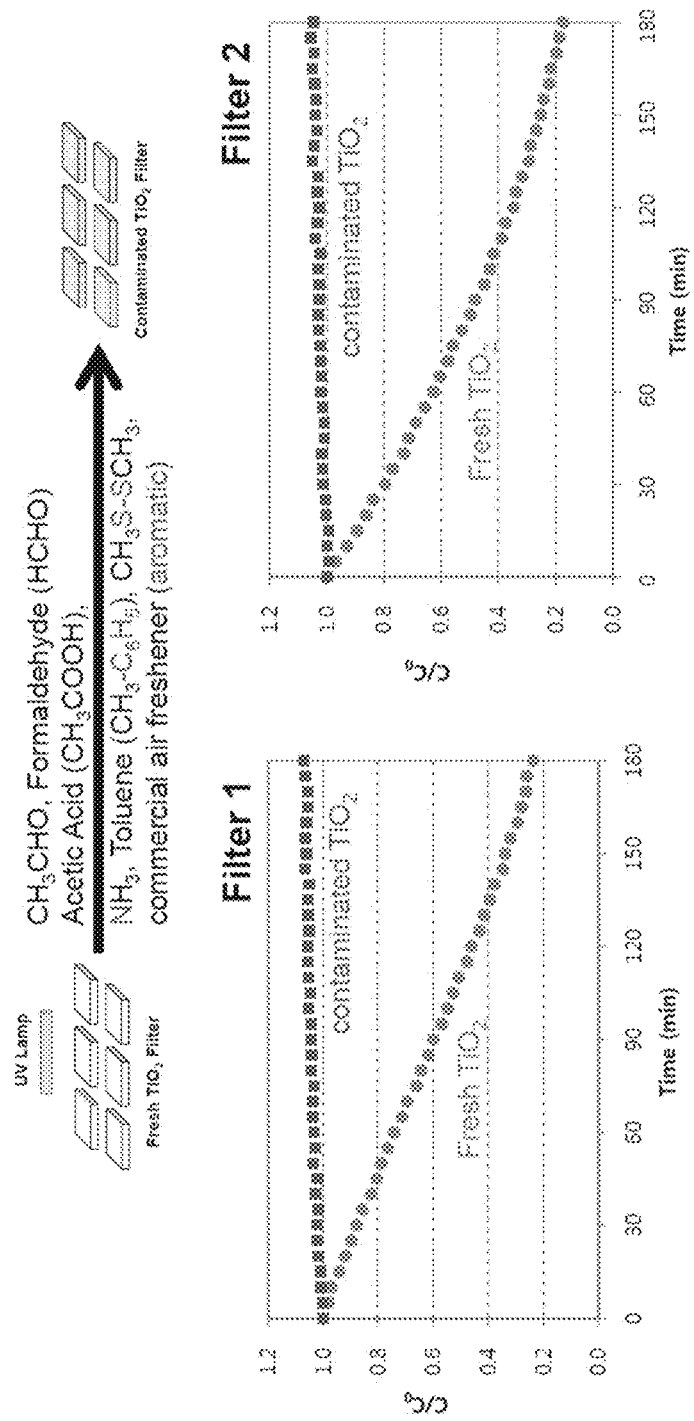
FIG. 9 is a graph showing the results of cleaning air by a photocatalytic filter before and after contamination of the filter.
Figure 10:
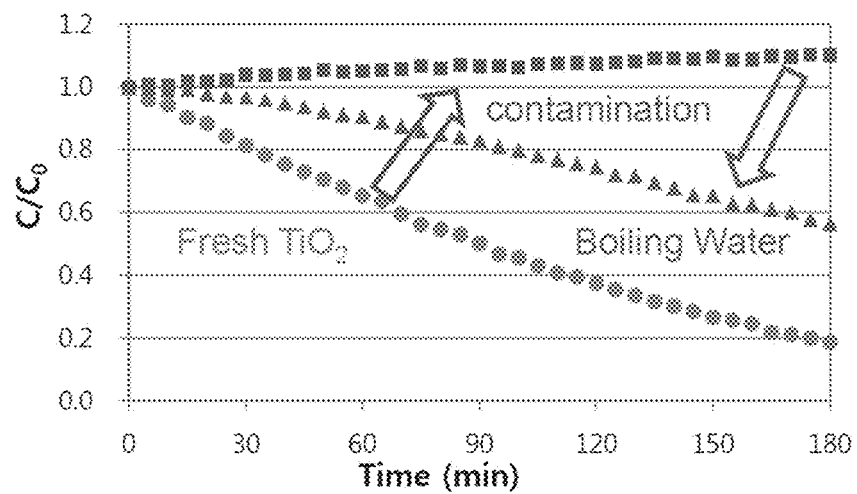
FIG. 10 is a graph showing the results of cleaning air by a photocatalytic filter before and after contamination of the filter and after reactivating the filter by treating the filter with boiling water.
Figure 11:
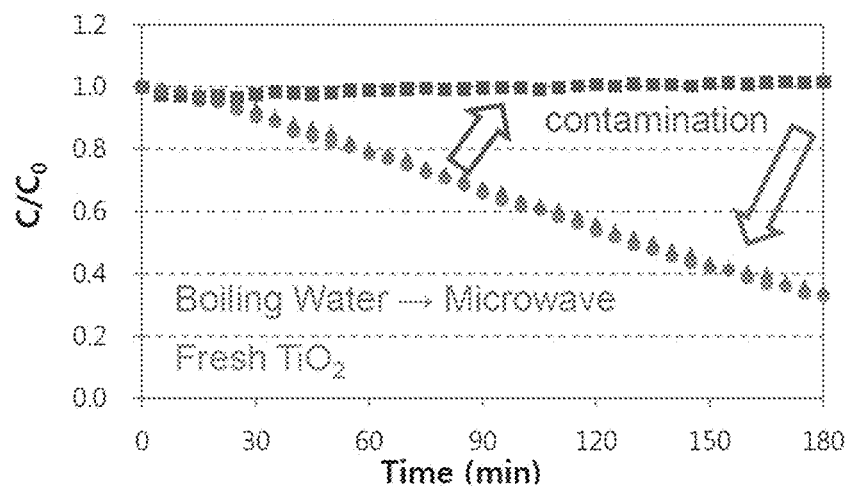
FIG. 11 is a graph showing the results of cleaning air by a photocatalytic filter before and after contamination of the filter and after reactivating the filter by treating the filter with boiling water and microwaving the treated filter.

The reactivative characteristics of the $TiO_2$ nanoparticle-coated photocatalyst are shown in FIG. 9 to FIG. 11. The two graphs (marked Filter 1 and Filter 2) on FIG. 9 show two sets of experiments to irradiate a contaminated $TiO_2$ nanoparticle coated filter and a fresh uncontaminated $TiO_2$ nanoparticle coated filter, by using a UV LED source for a period of 3 hours so as to remove acetaldehyde. In both Filter 1 and Filter 2 figures, the contaminated $TiO_2$ nanoparticle coated filter is contaminated with chemicals including formaldehyde, acetic acid, $NH_3$, toluene, $CH_3$—S—$SCH_3$, or commercial air freshener (aromatic).

As can be seen in FIG. 9, the uncontaminated filter normally degraded acetaldehyde (see the plot marked as Fresh $TiO_2$ in FIG. 9). However, when an experiment was performed using a photocatalytic filter contaminated after used in the above-described acetaldehyde removal experiment, it could be seen that the amount of acetaldehyde did not decrease (see the plot marked as contaminated TiO₂ in FIG. 9), suggesting that the photocatalytic activity of the filter was poor.

FIG. 10 shows reactivation of the contaminated TiO₂ nanoparticle coated on filters after being treated with boiling water and FIG. 11 shows reactivation of the contaminated TiO₂ nanoparticle coated on filters after being treated a combination of boiling water and microwave exposure. The reactivity properties of the contaminated TiO₂ nanoparticle coated on filters are compared against fresh uncontaminated TiO₂ nanoparticle coated on filters.

As can be seen in FIG. 10, when the contaminated filter was treated with boiling water, the function of the filter was significantly restored. As shown in FIG. 11, when the contaminated filter was treated with boiling water and then microwaved, the filter was reactivated so that it would show performance nearly similar to that of its original state.

As described above, the present disclosure provides the photocatalytic filter including the photocatalytic material attached securely to the support. Thus, the photocatalytic material is not detached from the photocatalytic filter during reactivation, and thus can be repeatedly reactivated. Thus, the photocatalytic filter can be used semi-permanently. This is different from The conventional photocatalytic filters where the reactivation via boiling cannot be achieved since the photocatalytic material is not so securely attached to the support as it is not eluted from the support into water while being treated with boiling water.

In addition, according to the present disclosure, the photocatalytic filter can be reactivated in a simple manner without using a troublesome washing process.

Though only a few embodiments, implementations and examples are described, other embodiments and implementations, and various enhancements and variations can be made based on what is described and illustrated in this document.

What is claimed is:

1. A method of manufacturing a photocatalytic filter, the method including:
    dispersing a photocatalytic material;
    coating a support with the dispersed photocatalytic material;
    drying the coated support; and
    sintering the dried support to provide a catalyst portion of the photocatalytic filter;
    wherein the catalyst portion has a height between 8 to 10 mm,
    wherein the photocatalytic filter includes cells formed in the catalyst portion and provides an air flow path in a direction facing UV LED for photocatalytic activation,
    wherein a frame between the cells has a thickness of 0.3 to 1.2 mm, and each of the cells has a width of 2 to 4 mm.

2. The method of claim 1, wherein the photocatalytic material includes titanium dioxide (TiO₂).

3. The method of claim 1, wherein the support includes porous ceramic.

4. The method of claim 1, wherein the sintering is performed for from one to three hours at a temperature between 400° C. and 500° C.

5. A photocatalytic filter, including:
    a catalyst portion including a porous ceramic support and dispersed TiO₂ nanoparticles coated on the porous ceramic support; and
    a bumper covering a side of the catalyst portion; and
    cells formed in the catalyst portion and providing an air flow path in a direction facing UV LED for photocatalytic activation,
    wherein the photocatalytic filter has a height between 8 to 10 mm,
    wherein a frame between the cells has a thickness of 0.3 to 1.2 mm, and
    wherein each of the cells has a width of 2 to 4 mm.

6. The photocatalytic filter of claim 5, wherein the TiO₂ nanoparticles are sintered for from one to three hours at a temperature between 400° C. and 500° C.

7. The method of claim 1, further comprising adding distilled water to the photocatalytic filter.

8. The method of claim 1, further comprising, after the covering of the side of the support:
    sonicating the photocatalytic filter.

9. The method of claim 8, wherein the photocatalytic material maintains an adhesion to the support while the photocatalytic filter is sonicated.

* * * * *